US009539218B2

(12) United States Patent
Misselwitz et al.

(10) Patent No.: US 9,539,218 B2
(45) Date of Patent: Jan. 10, 2017

(54) PREVENTION AND TREATMENT OF THROMBOEMBOLIC DISORDERS

(75) Inventors: Frank Misselwitz, Heidelberg (DE); Dagmar Kubitza, Ratingen (DE); Son-Mi Park, Wuppertal (DE); Klaus Wehling, Wuppertal (DE)

(73) Assignee: BAYER INTELLECTUAL PROPERTY GMBH, Monheim am Rhein (DE)

(*) Notice: Subject to any disclaimer, the term of this patent is extended or adjusted under 35 U.S.C. 154(b) by 2951 days.

(21) Appl. No.: 11/883,218

(22) PCT Filed: Jan. 19, 2006

(86) PCT No.: PCT/EP2006/000431
§ 371 (c)(1),
(2), (4) Date: Jul. 16, 2008

(87) PCT Pub. No.: WO2006/079474
PCT Pub. Date: Aug. 3, 2006

(65) Prior Publication Data
US 2009/0004265 A1    Jan. 1, 2009

(30) Foreign Application Priority Data
Jan. 31, 2005  (EP) .................................... 05001893

(51) Int. Cl.
*A61K 31/00*    (2006.01)
*A61K 31/5377*  (2006.01)

(52) U.S. Cl.
CPC ........... *A61K 31/00* (2013.01); *A61K 31/5377* (2013.01)

(58) Field of Classification Search
CPC ............................ A61K 31/00; A61K 31/5377
See application file for complete search history.

(56) References Cited

U.S. PATENT DOCUMENTS

| | | | |
|---|---|---|---|
| 2,811,555 A | 10/1957 | Larive et al. |
| 3,279,880 A | 10/1966 | Straley et al. |
| 4,128,654 A | 12/1978 | Fugitt et al. |
| 4,250,318 A | 2/1981 | Dostert et al. |
| 4,327,725 A | 5/1982 | Cortese et al. |
| 4,500,519 A | 2/1985 | Lormeau et al. |
| 4,705,779 A | 11/1987 | Madi-Szabo et al. |
| 4,765,989 A | 8/1988 | Wong et al. |
| 4,948,801 A | 8/1990 | Carlson et al. |
| 4,977,173 A | 12/1990 | Brittelli et al. |
| 5,002,937 A | 3/1991 | Bosies et al. |
| 5,254,577 A | 10/1993 | Carlson et al. |
| 5,349,045 A | 9/1994 | Jiang |
| 5,532,255 A | 7/1996 | Raddatz et al. |
| 5,561,148 A | 10/1996 | Gante et al. |
| 5,565,571 A | 10/1996 | Barbachyn et al. |
| 5,654,428 A | 8/1997 | Barbachyn et al. |
| 5,654,435 A | 8/1997 | Barbachyn et al. |
| 5,688,792 A | 11/1997 | Barbachyn et al. |
| 5,756,732 A | 5/1998 | Barbachyn et al. |
| 5,792,765 A | 8/1998 | Riedl et al. |
| 5,801,246 A | 9/1998 | Barbachyn et al. |
| 5,827,857 A | 10/1998 | Riedl et al. |
| 5,910,504 A | 6/1999 | Hutchinson et al. |
| 5,922,708 A | 7/1999 | Riedl et al. |
| 5,929,248 A | 7/1999 | Barbachyn et al. |
| 5,935,724 A | 8/1999 | Spillman et al. |
| 5,972,947 A | 10/1999 | Tsaklakidis et al. |
| 5,977,373 A | 11/1999 | Gadwood et al. |
| 5,998,406 A | 12/1999 | Hester et al. |
| 6,069,160 A | 5/2000 | Stolle et al. |
| 6,159,997 A | 12/2000 | Tsujita et al. |
| 6,218,413 B1 | 4/2001 | Hester et al. |
| 6,251,869 B1 | 6/2001 | Bohanon |
| 6,265,178 B1 | 7/2001 | Martin, Jr. |
| 6,281,210 B1 | 8/2001 | Hester, Jr. |
| 6,294,201 B1 | 9/2001 | Kettelhoit et al. |
| 6,805,881 B1 | 10/2004 | Kanikanti et al. |
| 6,818,243 B2 | 11/2004 | Nagashima et al. |
| 7,034,017 B2 | 4/2006 | Straub et al. |
| 7,045,631 B2 | 5/2006 | Straub et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,157,456 B2 | 1/2007 | Straub et al. |
| 2001/0029351 A1 | 10/2001 | Falotico et al. |
| 2001/0046987 A1 | 11/2001 | Hester et al. |

(Continued)

FOREIGN PATENT DOCUMENTS

| | | |
|---|---|---|
| AU | 744002 | 2/2002 |
| DE | 2836305 A1 | 3/1979 |
| DE | 196 04 223 A1 | 8/1997 |
| DE | 19962924 A1 | 7/2001 |
| DE | 10105989 A1 | 8/2002 |
| DE | 10129725 A1 | 1/2003 |
| DE | 10355461 A1 | 6/2005 |
| EP | 0 127 902 A2 | 12/1984 |
| EP | 0 316 594 A1 | 5/1989 |
| EP | 0 352 781 A2 | 1/1990 |
| EP | 0350002 A1 | 1/1990 |
| EP | 0623615 A1 | 11/1994 |
| EP | 0645376 A1 | 3/1995 |
| EP | 0738726 A1 | 10/1996 |
| EP | 0 785 200 A2 | 7/1997 |

(Continued)

OTHER PUBLICATIONS

White, R.H., "The Epidemiology of Venous Thromboembolism", Circulation, (2003), vol. 107, (Suppl. 1), pp. I-4-I-8.

(Continued)

*Primary Examiner* — Sreeni Padmanabhan
*Assistant Examiner* — Jody Karol
(74) *Attorney, Agent, or Firm* — Buchanan Ingersoll & Rooney PC

(57) ABSTRACT

The present invention relates to the field of blood coagulation, more specifically it relates to a method of treating a thromboembolic disorder by administering once daily a direct factor Xa inhibitor in oral dosage form to a patient in need thereof, wherein the factor Xa inhibitor has a plasma concentration half life indicative of a bid or tid administration interval, e.g. of 10 hours or less.

4 Claims, No Drawings

(56) References Cited

U.S. PATENT DOCUMENTS

| | | | |
|---|---|---|---|
| 2003/0153610 A1 | 8/2003 | Straub et al. | 514/376 |
| 2003/0161882 A1 | 8/2003 | Waterman | |
| 2004/0162427 A1 | 8/2004 | Rosentreter et al. | |
| 2004/0242660 A1 | 12/2004 | Straub et al. | |
| 2005/0064006 A1 | 3/2005 | Perzborn et al. | |
| 2005/0182055 A1 | 8/2005 | Berwe et al. | |
| 2005/0261502 A1 | 11/2005 | Straub et al. | |
| 2006/0154969 A1 | 7/2006 | Rosentreter et al. | |
| 2006/0258724 A1 | 11/2006 | Straub et al. | |
| 2007/0026065 A1 | 2/2007 | Benke et al. | |
| 2007/0149522 A1 | 6/2007 | Thomas | |
| 2008/0026057 A1 | 1/2008 | Benke | |
| 2008/0090815 A1 | 4/2008 | Straub et al. | |
| 2008/0200674 A1 | 8/2008 | Straub et al. | |

FOREIGN PATENT DOCUMENTS

| | | |
|---|---|---|
| EP | 0930076 A1 | 7/1999 |
| EP | 0950386 A2 | 10/1999 |
| GB | 2140687 | 12/1984 |
| WO | WO-93/09103 A1 | 5/1993 |
| WO | WO-93/23384 A1 | 11/1993 |
| WO | WO-97/03072 A1 | 1/1997 |
| WO | WO-97/09328 A1 | 3/1997 |
| WO | WO-97/10223 A1 | 3/1997 |
| WO | WO-98/01446 A1 | 1/1998 |
| WO | WO-98/54161 A1 | 12/1998 |
| WO | WO-99/02525 A1 | 1/1999 |
| WO | WO-99/03846 A1 | 1/1999 |
| WO | WO-99/06371 A1 | 2/1999 |
| WO | WO-99/21535 A1 | 5/1999 |
| WO | WO-99/24428 A1 | 5/1999 |
| WO | WO-99/29688 A1 | 6/1999 |
| WO | WO-99/31092 A1 | 6/1999 |
| WO | WO-99/37304 A1 | 7/1999 |
| WO | WO-99/37630 A1 | 7/1999 |
| WO | WO-99/40094 A1 | 8/1999 |
| WO | WO-99/59616 A1 | 11/1999 |
| WO | WO-00/16748 A1 | 3/2000 |
| WO | WO-01/42242 A1 | 6/2001 |
| WO | WO-01/44212 A1 | 6/2001 |
| WO | WO-01/46185 A1 | 6/2001 |
| WO | WO-01/47919 A1 | 7/2001 |
| WO | WO-01-47949 A1 | 7/2001 |
| WO | WO-02/25210 A1 | 3/2002 |
| WO | WO-02/064575 A1 | 8/2002 |
| WO | WO-02/070484 A1 | 9/2002 |
| WO | WO-02/070485 A1 | 9/2002 |
| WO | WO-02/070520 A1 | 9/2002 |
| WO | WO-02/079195 A1 | 10/2002 |
| WO | WO-02/079196 A1 | 10/2002 |
| WO | WO-03/000256 A1 | 1/2003 |
| WO | WO-03/008384 A1 | 1/2003 |
| WO | WO-03/035133 A1 | 5/2003 |
| WO | WO-03/053441 A1 | 7/2003 |
| WO | WO-2004/060887 A1 | 7/2004 |
| WO | WO-2005/060940 A1 | 5/2005 |
| WO | WO-2005/068456 A1 | 7/2005 |
| WO | WO-2006/072367 A1 | 7/2006 |
| WO | WO-2006/079474 A1 | 8/2006 |
| WO | WO-2007/036306 A1 | 4/2007 |
| WO | WO-2007/039122 A2 | 4/2007 |
| WO | WO-2007/039132 A1 | 4/2007 |
| WO | WO-2007/039134 A1 | 4/2007 |
| WO | WO-2007/042146 A1 | 4/2007 |
| WO | WO-2008/012002 A1 | 1/2008 |
| WO | WO-2008/052671 A1 | 5/2008 |

OTHER PUBLICATIONS

Feign, V.L., et al., "Stroke Epidemiology: A Review of Population-Based Studies of Incidence, Prevalence, and Case-Fatality in the Late 20th Century", The Lancet Neurology, (2003), vol. 2, pp. 43-53.

Fang, J., et al., "Dissociation of Hospitalization and Mortality Trends for Myocardial Infarction in the United States from 1988 to 1997", The American Journal of Medicine, (2002), vol. 113, pp. 208-214.

Raghaven, S.A.V., et al., "Recent Advances in the Status and Targets of Antithrombotic Agents", Drugs of the Future, (2002), Vo.. 27, No. 7, pp. 669-683.

Wieland, H.A., et al., "Approaches in Anticoagulation: Rationales for Target Positioning", Current Opinion in Investigational Drugs, (2003), vol. 4, No. 3. pp. 264-271.

Ries, U.J., et at., "Serine Proteases as Targets for Antithrombotic Therapy", Drugs of the Future, (2003), vol. 28, No. 4, pp. 355-370.

Linkins, L-A., et al., "New Anticoagulant Therapy", Annu. Rev. Med., (2005), vol. 56, pp. 63-77.

Goodman and Gillman, "The Pharmacological Basis of Therapeutics", 7th Ed., MacMillian Publishing Co., NY, (1985), pp. 27-28.

Rowland, M., et al., "Multiple-Dose Regimens", Clinical Pharmacokinetics, Concepts and Applications, 3rd Ed, Lea & Febiger, Williams & Wilkins, Media, PA (1995), pp. 83-105.

Birkett, D.J., "Why is Half-Life Important", Pharmacokinetics Made Easy, McGraw-Hill Education, (2000), pp. 20-21.

Roehrig, S., et al., "Discovery of the Novel Antithrombotic Agent Bay 59-7939, an Orally Active, Direct Factor XA Inhibitor", 228th ACS National Meeting, (2004), MEDI-156.

Geerts, W.H., et al., "Prevention of Venous Thromboembolism", Chest, (2001), vol. 119, pp. 132S-175S.

Takehana, S., et al., "Antithrombotic Effect of AX1826, A Novel Inhibitor of Factor Xa, in the Rat Thrombosis Models", Japanese Journal of Pharmacology, (2000), 82 (Suppl. 1), 213P.

Just, M., et al., "A Comparison of a Specific Factor Xa Inhibitor (HMR-2906) and Recombinant Hirudin in a Dog Coronary Artery Thrombosis Model", XVIIth Congress of the International Society for Thrombosis and Haemostasis, Washington, D.C., (1999).

Chu, V., et al., "Pharmacological Characterization of a Novel Factor Xa Inhibitor, FXV673", Thrombosis Research, (2001), vol. 103, pp. 309-324.

Guertin, K.R., et al., "Optimization of the β-Aminoester Class of Factor Xa Inhibitors. Part 2: Identification of FXV673 as a Potent and Selective Inhibitor with Excellent In Vivo Anticoagulant Activity", Bioorganic & Medicinal Chemistry Letters, (2002), vol. 12, pp. 1671-1674.

Ries, U.J., et al., "Heterocyclic Coagulation Inhibitors: Design and Synthesis of Dual Direct Thrombin and Factor Xa Inhibitors", American Chemical Society—226th National Meeting, (2003).

Pruitt, James R., et al., "Discovery of 1-(2-Aminomethylphenyl)-3-trifluoromethyl-N-[3-fluoro-2'-(aminosulfonyl)[1,1'-biphenyl)]-4-yl]-1 H-pyrazole-5-carboxyamide (DPC602), a Potent, Selective, and Orally Bioavailable Factor Xa Inhibitor", J. Med. Chem., (2003), vol. 46, No. 25, pp. 5298-5315.

Nagahara, T., et al., "Dibasic (Amidinoraryl)propanoic Acid Derivatives as Novel Blood Coagulation Factor Xa Inhibitors", J. Med. Chem., (1994), vol. 37, No. 8, pp. 1200-1207.

Morishima, Y., et al., "In Vitro Characteristics, Anticoagulant Effects and In Vivo Antithrombotic Efficacy of a Novel, Potent and Orally Active Direct Factor Xa Inhibitor, DU-176b", Blood, (2004), (Abst 1862).

Fukuda, T., et al., "Antithrombotic Properties of DU-176b, a Novel, Potent and Orally Active Direct Factor Xa Inhibitor in Rat Models of Arterial and Venous Thrombosis: Comparison with Fondaparinux, an Antithrombin Dependent Factor Xa Inhibitor", Blood, (2004), (Abst 1852).

Furugohri, T., et al, "Antithrombotic and Hemorrhagic Effects of DU-176b, a Novel, Potent and Orally Active Direct Factor Xa Inhibitor: A Wider Safety Margin Compared to Heparins and Warfarin", Blood, (2004), (Abst. 1851).

Proteinase 2004: Strategies for New Medicines, 4th SCI-RSC Symposium, Proteinase Inhibitor Design, (2004).

Koizumi, T. et al., "Effect of KFA-1982, a New Orally Active Factor Xa Inhibitor, in a Rabbit Venous Thrombosis Model", J. of Thrombosis and Haemostasis, vol. 1, Suppl. 1, (2003), p. 2022. (abstract).

(56) References Cited

OTHER PUBLICATIONS

Nishida, H., et al., "Synthesis and Evaluation of 1-Arylsulfonyl-3-piperazinone Derivatives as Factor Xa Inhibitors[1,2] III. Effect of Ring Opening of Piperazinone Moiety on Inhibition", Chem. Pharm. Bull., (2004), vol. 52, No. 4. pp. 459-462.
Nishida, H., et al., "Synthesis and Evaluation of 1-Arylsulfonyl-3-piperazinone Derivatives as Factor Xa Inhibitors [1-3]) IV. A Series of New Derivatives Containing a Spiro [5H-oxazolo[3,2-a]pyrazine-2(3H),4'-piperidin]-5-one Skeleton", Chem. Pharm. Bull., (2004), vol. 52, No. 4, pp. 406-412.
Nishida, H., et al., "Synthesis and Evaluation of 1-Arylsulfonyl-3-piperazinone Derivatives as a Factor Xa Inhibitor[1,2]) II. Substituent Effect on Biological Activities", Chem. Pharm. Bull., (2002), vol. 50, No. 9, pp. 1187-1194.
Nishida, H., et al., "Synthesis and Evaluation of 1-Arylsulfonyl-3-piperazinone Derivatives as Factor Xa Inhibitor", Chem. Pharm. Bull. vol. 49, No. 10, (2001), pp. 1237-1244.
Young, S. C., "Factor Xa Inhibitor LY517717; A Novel and Effective Oral Anticoagulant", Medicinal Chemistry—12th RSC-SCI Symposium, Sep. 7-10, 2003, Cambridge, UK.
M. Wiley, et al., 228th ACS National Meeting, Philadelphia, Aug. 22-26, 2004, MEDI-252 & 254.
Nishida, H. et al., "Design Synthesis and Biological Activities of New Potent Factor Xa Inhibitor," 228th ACS National Meeting, Philadelphia, Aug. 22-26, 2004, Slides from MED1-251.
Research and Development Pipeline, Yamanouchi Pharmaceutical Co. Ltd., Company World Wide Web site, "Yamanouchi and Fujisawa Enter Into a Basic Agreement to Merge on Apr. 1, 2005", (2004), 7 pages.
Nazaré, M., et al., "Novel Factor Xa Inhibitors Based on a 2-Carboxyindole Scaffold: SAR of P4 Substituents in Combination With a Neutral P1 Ligand", Bioorganic & Medicinal Chemistry Letters, vol. 14, (2004), pp. 4197-4201.
Nazaré, M., "Novel Factor Xa Inhibitors Based on a Benzoic Acid Scaffold and Incorporating a Neutral P1 Ligand", Bioorganic & Medicinal Chemistry Letters, vol. 14, (2004), pp. 2801-2805.
Choi-Sledeski, Y. M., et al., "Discovery of an Orally Efficacious Inhibitor of Coagulation Factor Xa Which Incorporates a Neutral P Ligand", Journal of Medicinal Chemistry, vol. 46, No. 5, (2003), pp. 681-684.
Maignan, S., et al., "Molecular Structures of Human Factor Xa Complexed with Ketopiperazine Inhibitors: Preference for a Neutral Group in the S1 Pocket", Journal of Medicinal Chemistry, vol. 46, No. 5, (2003), pp. 685-690.
Adler, M., et al., "Crystal Structures of Two Potent Nonamidine Inhibitors Bound to Factor Xa", Biochemistry, vol. 41, No. 52,(2002), pp. 15514-15523.
Chou, Y.-L., et al., "Structure-Activity Relationships of Substituted Benzothiophene-Anthranilamide Factor Xa Inhibitors", Bioorganic & Medicinal Chemistry Letters, vol. 13, (2003), pp. 507-511.
Quan, M. L., et al., "Discovery of 1-(3'-Aminobenzisoxazol-5'-yl)-3-Trifluoromethyl-N-[2-Fluoro-4-[(2'-Dimethylaminomethyl)Imidazol-1-yl]Phenyl]-1H-Pyrazole-5-Carboxyamide Hydrochloride (Razaxaban), a Highly Potent, Selective, and Orally Bioavailable Factor Xa Inhibitor", Journal of Medicinal Chemistry, vol. 48, No. 6, (2005), pp. 1729-1744.
Pinto, D. J.P., et al., "Discovery of 1-[3-(Aminomethyl)Phenyl]-N-[3-Fluoro-2'-(Methylsulfonyl)-[1,1'-Biphenyl]-4-yl]-3-(Trifluoromethyl)[1H-Pyrazole-5-Carboxamide (DPC423), a Highly Potent, Selective, and Orally Bioavailable Inhibitor of Blood Coagulation Factor Xa", Journal of Medicinal Chemistry, vol. 44, No. 4, (2001), pp. 566-578.
Haginoya, N., et al., "Synthesis and Conformational Analysis of a Non-Amidine Factor Xa Inhibitor That Incorporates 5-Methyl-4,5,6,7-Tetrahydrothiazolo[5,4-c]Pyridine as S4 Binding Element", Journal of Medicinal Chemistry, vol. 47, No. 21, (2004), pp. 5167-5182.
Mederski, W., et al., "Halothiophene Benzimidazoles as P1 Surrogates of Inhibitors of Blood Coagulation Factor Xa", Bioorganic & Medicinal Chemistry Letters, vol. 14, (2004), pp. 3763-3769.

Zhang, P., et al., "Design, Synthesis, and SAR of Anthranilamide-Based Factor Xa Inhibitors Incorporating Substituted Biphenyl P4 Motifs", Bioorganic & Medicinal Chemistry Letters, vol. 14, (2004), pp. 983-987.
Zhang, P., "Design, Synthesis, and SAR of Anthranilamide-based Factor Xa Inhibitors with Improved Functional Activity", Bioorganic & Medicinal Chemistry Letters, vol. 14, (2004), pp. 989-993.
Willardsen, J. A., et al., "Design, Synthesis, and Biological Activity of Potent and Selective Inhibitors of Blood Coagulation Factor Xa", Journal of Medicinal Chemistry, vol. 47, No. 16, (2004), pp. 4089-4099.
Kubitza, et al., Multiple dose escalation study investigating the pharmacodyanamics, safety, and pharmacokinetics of BAY 59-7939 an oral, direct Factor Xa inhibitor in healthy male subjects, Blood, vol. 102:11, Nov. 16, 2003, p. 811a.
Kubitza, et al., Abstract 3010, Single dose escalation study investigating the pharmacodyanamics, safety, and pharmacokinetics of BAY 59-7939 an oral, direct Factor Xa inhibitor in healthy male subjects, Blood, vol. 102:11, Nov. 16, 2003, p. 813a.
Bono, F., et al., "Human Umbilical Vein Endothelial Cells Express High Affinity Receptors for Factor Xa", Journal of Cellular Physiology, 1997, vol. 172, pp. 36-43.
Cocks, T. M., et al., "Protease-Activated Receptors: Sentries for Inflammation", Tips, 2000, vol. 21, pp. 103-108.
Ross, R., "Atherosclerosis—An Inflammatory Disease", New England J. of Medicine, 1999, vol. 340, No. 2, pp. 115-126.
Nakata, M., et al., "DX9065a an Xa Inhibitor, Inhibits Prothrombin-Induced A549 Lung Adenocarcinoma Cell Proliferation", Cancer Letters, 1998, vol. 122, pp. 127-133.
Kaiser, B., et al., "A Synthetic Inhibitor of Factor Xa, DX-9065a, Reduces Proliferation of Vascular Smooth Muscle Cells in Vivo in Rats", Thrombosis Research, 2000, vol. 98, pp. 175-185.
Altieri, D. C., et al., "Identification of Effector Cell Protease Receptor-1", The Journal of Immunology, 1990, vol. 145, No. 1, pp. 246-253.
Coughlin, S. R., "Thrombin Signalling and Protease-Activated Receptors", Nature, 2000, vol. 407, pp. 258-264.
Ornstein, D. L., et al., "Cancer, Thrombosis, and Anticoagulants", Current Opinion in Pulmonary Medicine, 2000, vol. 6, pp. 301-308.
Dabbagh, K., et al., "Thrombin Stimulates Smooth Muscle Cell Procollagen Synthesis and mRNA Levels via a PAR-1 Mediated Mechanism", Thrombasis and Haemostasis, vol. 79, No. 2 1997, pp. 405-409.
Herault, J-P., et al., "Activation of Human Vascular Endothelial Cells by Factor Xa: Effect of Specific Inhibitors", Biochemical Pharmacology, 1999, vol. 57, pp. 603-610.
Leveugle, B., et al., "Heparin Oligosaccharides that Pass the Blood-Brain Barrier Inhibit β-Amyloid Precursor Protein Secretion and Heparin Binding to β-Amyloid Peptide", Journal of Neurochemistry, 1998, vol. 70, No. 2, pp. 736-744.
Molino, M., et al., "Differential Expression of Functional Protease-Activated Receptor-2 (PAR-2) in Human Vascular Smooth Muscle Cells", Arteriosclerosis, Thrombasis, and Vascular Biology, vol. 18, No. 5, 1998, pp. 825-832.
Plescia, J., et al., "Activation of MAC-1 (CD11b/CD18)-Bound Factor X by Release Cathepsin G Defines an Alternative Pathway of Leucocyte Initiation of Coagulation", Biochem. J., 1996, vol. 319, pp. 873-879.
Howells, G. L., et al., "Proteinase-Activated Receptor-2: Expression by Human Neutrophils", Journal of Cell Science, 1997, vol. 110, pp. 881-887.
Herbert, J.-M., et al., "Effector Protease Receptor 1 Mediates the Mitogenic Activity of Factor Xa for Vascular Smooth Muscle Cells in Vitro and In Vivo", J. Clin. Invest., 1998, vol. 101, No. 5, pp. 993-1000.
Donnelly, K. M., et al., "*Ancylostoma caninum* Anticoagulant Peptide Blocks Metastasis In Vivo and Inhibits Factor Xa Binding to Melanoma Cells In Vitro", Thromb Haemost, 1998, vol. 79, pp. 1041-1047.

(56) References Cited

OTHER PUBLICATIONS

Ragosta, M., et al., "Specific Factor Xa Inhibition Reduces Restenosis After Balloon Angioplasty of Atherosclerotic Femoral Arteries in Rabbits", Circulation, 1994, vol. 89, No. 3, pp. 1262-1271.
Zhang, Y., et al., "Tissue Factor Controls the Balance of Angiogenic and Antiangiogenic Properties of Tumor Cells in Mice", J. Clin. Invest., 1994, vol. 94, pp. 1320-1327.
Green, D., et al., "Lower Mortality in Cancer Patients Treated with Low-Molecular-Weight Versus Standard Heparin", The Lancet, 1992, vol. 339, p. 1476.
Ko, F. N., et al., "Coagulation Factor Xa Stimulates Platelet-Derived Growth Factor Release and Mitogenesis in Cultured Vascular Smooth Muscle Cells of Rat", J. Clin. Invest., 1996, vol. 98, No. 6, pp. 1493-1501.
Kakkar, A. K., et al., "Antithrombotic Therapy in Cancer", BMJ, 1999, vol. 3318, pp. 1571-1572.
Gasic, G. P., et al., "Coagulation Factors X, Xa, and Protein S as Potent Mitogens of Cultured Aortic Smooth Muscle Cells", Proc. Natl. Acad. Sci. USA, 1992, vol. 89, pp. 2317-2320.
Cirino, G., et al., "Factor Xa as an Interface Between Coagulation and Inflammation: Molecular Mimicry of Factor Xa Association with Effector Cell Protease Receptor-1 Induces Acute Inflammation In Vivo", J. Clin. Invest., 1997, vol. 99, No. 10, pp. 2446-2451.
Senden, N. H. M., et al., "Factor Xa Induces Cytokine Production and Expression of Adhesion Molecules by Human Umbilical Vein Endothelial Cells", The Journal of Immunology, 1998, vol. 161, pp. 4318-4324.
Papapetropoulos, A., et al., "Hypotension and Inflammatory Cytokine Gene Expression Triggered by Factor Xa-Nitric Oxide Signaling", Proc. Natl. Acad. Sci. USA, 1998, vol. 95, pp. 4738-4742.
Camerer, E., et al., "Tissue Factor- and Factor X-dependent Activation of Protease-Activated Receptor 2 by Factor VIIa", PNAS, 2000, vol. 97, No. 10, pp. 5255-5260.
Donovan, F. M., et al., "Thrombin Induces Apoptosis in Cultured Neurons and Astrocytes via a Pathway Requiring Tyrosine Kinase and RhaA Activities", The Journal of Neuroscience, 1997, vol. 17, No. 14, pp. 5316-5326.
Lindner, J. R., et al., "Delayed Onset of Inflammation in Protease-Activated Receptor-2-Deficient Mice", The Journal of Immunology, 2000, pp. 6504-6510.
Bouchard, B. A., et al., "Effector Cell Protease Receptor-1, a Platelet Activation-dependent Membrane Protein, Regulates Prothrombinase-catalyzed Thrombin Generation", The Journal of Biological Chemistry, 1997, vol. 272, No. 14, pp. 9244-9251.
Molino, M., et al., "Endothelial Cell Thrombin Receptors and PAR-2", The Journal of Biological Chemistry, 1997, vol. 272, No. 17, pp. 11133-11141.
Nicholson, A. C., et al., "Effector Cell Protease Receptor-1 Is a Vascular Receptor for Coagulation Factor Xa", The Journal of Biological Chemistry, 1996, vol. 271, No. 45, pp. 28407-28413.
Watson, D. J., et al., "Heparin-Binding Properties of the Amyloidogenic Peptides Aβ and Amylin", The Journal of Biological Chemistry, 1997, vol. 272, No. 50, pp. 31617-31624.
Tuszynski, G. P., et al., "Isolation and Characterization of Antistasin", The Journal of Biological Chemistry, 1987, vol. 262, No. 20, pp. 9718-9723.
Kranzhöfer, R., et al., "Thrombin Potently Stimulates Cytokine Production in Human Vascular Smooth Muscle Cells but Not in Mononuclear Phagocytes", Circulation Research, 1996, vol. 79, No. 2, pp. 286-294.
Schwartz, R. S., et al., "Neointimal Thickening After Severe Coronary Artery Injury is Limited by Short-term Administration of a Factor Xa Inhibitor", Circulation, 1996, vol. 93, No. 8, pp. 1542-1548.
Abendschein, D. R., et al., "Inhibition of Thrombin Attenuates Stenosis After Arterial Injury in Minipigs", JACC, 1996, vol. 28, No. 7, pp. 1849-1855.
Carmeliet, P., et al., "Gene Manipulation and Transfer of the Plasinogen and Coagulation System in Mice", Seminars in Thrombosis and Hemostasis, 1996, vol. 22, No. 6, pp. 525-542.
Stouffer, G. A., et al., "The Role of Secondary Growth Factor Production in Thrombin-Induced Proliferation of Vascular Smooth Muscle Cells", Seminars in Thrombosis and Hemostasis, 1998, vol. 24, No. 2, pp. 145-150.
Bevilacqua, M. P., et al., "Inducible Endothelial Functions in Inflammation and Coagulation", Seminars in Thrombosis and Hemostasis, 1987, vol. 13, No. 4, pp. 425-433.
Riedl, B., et al., "Recent Developments with Oxazolidinone Antibiotics", Exp. Opin. Ther. Patents, 1999, vol. 9, No. 5, pp. 625-633.
Barbachyn, M.R., et al., "Identification of Novel Oxazolidinone (U-100480) with Potent Antimycobacterial Activity", J. Med. Chem., 1996, vol. 39, pp. 680-685.
Tucker, J. A., et al, "Piperazinyl Oxazolidinone Antibacterial Agents Containing a Pyridine, Diazene, or Triazene Heteroaromatic Ring", J. Med. Chem. 1998, vol. 41, pp. 3727-3735.
Brickner, S.J., et al., "Synthesis and Antibacterial Activity of U-100592 and U-100766, Two Oxazolidinone Antibacterial Agents for the Potenial treatment of Multidrug-Resistant Gram-Positive Bacterial Infections" J. Med. Chem., 1996, vol. 39, pp. 673-679.
Gregory, W.A., et al., "Antibacterials. Synthesis and Structure-Activity Studies of 3-Aryl-2-oxooxazolidines. 1. The "B" Group", J. Med. Chem., 1989, vol. 32, No. 8, pp. 1673-1681.
Berry, C. N., et al., "Antithrombotic Actions of Argatroban in Rat Models of Venous, 'Mixed' and Arterial Thrombosis, and its Effects on the Tail Transection Bleeding Time", Br. J. Pharmacol., 1994, vol. 113, pp. 1209-1214.
Meng, K., et al., "Effect of Acetylsalicyclic Acid of Experimentally Induced Arterial Thrombosis in Rats", Naunyn-Schmiedeberg's Arch. Pharmacol.,1977, vol. 301, pp. 115-119.
Chern, J.W., et al., "Studies on Quinazolines IX:[1] Fluorination Versus 1,2-Migration on the Reaction of 1,3-Bifunctionalized Amino-2-Propanol with DAST", Tetrahedron Lett., 1998, vol. 39, pp. 8483-8486.
Shakespeare, W. C., et al., "Palladium-Catalyzed Coupling of Lactams with Bromobenzenes", Tetrahedron Lett., 1999, vol. 40, pp. 2035-2038.
Renger, B., et al., "Direkte N-Arylierung von Amiden: Eine Verbesserung der Goldberg-Reaktion", Synthesis, 1985, pp. 856-860.
Aebischer, E., et al., "Synthesis of N-Arylrolipram Derivatives—Potent and Selective Phosphodiesterase-IV Inhibitors—by Copper Catalyzed Lactam-Aryl Halide Coupling", Hetercycles, 1998, vol. 48, No. 11 , pp. 2225-2229.
Pfeil, E., et al., "β-Aminoäthylierung von Indol und 2-methylindol", Angew Chem., 1967, vol. 79, No. 4, pp. 188-189.
Ziegler, C. B., et al., "Synthesis of Some Novel 7-Substituted Quinolonecarboxylic Acids via Nitroso and Nitrone Cycloadditions", J. Hetercycl. Chem., 1988, vol. 25, No. 2, pp. 719-723.
Bartoli, G., et al, "Electronic and Steric Effects in Nucleophilic Aromatic Substitution. Reaction by Phenoxides as Nucleophiles in Dimethyl Sulfoxide", J. Org. Chem., 1975, vol. 40, No. 7, pp. 872-874.
Reppe, et al., "N-p-Merthoxyphenyl-pyrrolidon", Justus Liebigs Ann. Chem., 1955 vol. 596, p. 208.
Luvalle, J.E., et al., "Oxidation Processes. XXI.[1] The Autoxidation of the p-Phenylenediamines", J. Am. Chem. Soc., 1948, vol. 70, pp. 2223-2233.
Snyder, H.R., et al., "Imidazo[4,5f]quinolines III: Antibacterial 7-Methyl-9-(substituted Arylamino)imidazo[4,5-f]quinolines", J. Pharm. Sci., 1977, vol. 66, pp. 1204-1406.
Adams, R., et al., "Sulfanilamide Derivatives. I", J. Am. Chem. Soc. 1939, vol. 61, pp. 2342-2349.
Khanna, I.K. , et al., "1,2-Diarylpyrroles as Potent and Selective Inhibitors of Cyclooxygenase-2", J. Med. Chem., 1997, vol. 40 , pp. 1619-1633.
Gutcait, A., et al., "Studies on Quinazolines. 6.[1] Asymmetric Synthesis of (S)-(+)- and (R)-(−)-3-[[4-(2-Methoxyphenyl)piperazin-1-yl]methylthio-2,3,-dihydromidazo[1,2-c]quinazolines", Tetrahedron Asym., 1996, vol. 7, No. 6, pp. 1641-1648.

(56) References Cited

OTHER PUBLICATIONS

Grell, W., et al., "Repaglinide and Related Hypoglycemic Benzoic Acid Derivatives", J. Med. Chem., 1998, vol. 41, pp. 5219-5246.
Artico, M. et al., "Rsearch on Compounds with Antiblastic Activity", Farmaco Ed. Sci. 1969, vol. 24, pp. 179-190.
Dankwardt, S. M., et al., "Nonpeptide Bradykinin Antagonist Analogs based on a Model of a Sterling-Winthrop Nonpeptide Bradykinin Antagonist Overlapped with Cyclic Hexapeptide Bradykinin Antagonist Peptides", Bioorg. Med. Chem. Lett., 1997, vol. 7, No. 14, pp. 1921-1926.
Reppe, et al., "N-6-Aminohexyl-pyrrolidon", Justus Liebigs Ann. Chem. 1955, vol. 596, pp. 204.
Bouchet, P., et al., "σ Values of N-Substitutes Azoles", J. Chem. Soc. Perkin Trans., 1974, vol. 2, pp. 449-451.
Surrey, A. R., et al., "The Preparation of N-Benzyl-3-Morpholones and N-Benzyl-3-Homomorpholones from N-(Hydroxyalkyl)-chloroacetamides" J. Amer. Chem. Soc., 1955, vol. 77, pp. 633-636.
Tong, L.K.J., et al., "The Mechanism of Dye Formation in Color Photography. VII. Intermediate Bases in the Deamination of Quinonediimines" J. Amer. Chem. Soc. 1960, vol. 82, 1988-2001.
Delande, S.A., "Heterocycles", Chemical Abstracts, American Chemical Society, 1979, vol. 90, pp. 663.
Bots, M., et al., Coagulation and Fibrinolysis Markers and Risk of Dementia, Haemostasis, vol. 28 (1998); pp. 216-222.
Benzakour, O., et al., "Cellular and molecular events in atherogenesis; basis for pharmocological and gene therapy approaches to stenosis," Cellular Pharmacology, 1996, vol. 3, pp. 7-22.
Kanthou, C., et al., "Cellular effects of thrombin and their signalling pathways," Cellular Pharmacology, vol. 2 (1995); pp. 293-302.
Kaiser, B., et al., "Antiproliferation Action of Factor Xa Inhibitors in a Rat Model of Chronic Restenosis," Abstracts of the XVIIth Congress of the International Society on Thrombosis and Haemostasis, Aug. 1999, p. 144.
Tyrrell, D., et al., "Heparin in Inflammation: Potential Therapeutic Applications Beyond Anticoagulation," Advances in Pharmacology, vol. 46 (1999); pp. 151-208.
Smirova, I., et al., "Thrombin Is an Extracellular Signal that Activates Intracellular Death Protease Pathways Inducing Apoptosis in Model Motor Neurons," J. Neurobiology, vol. 36 (1998); pp. 64-80.
Bono, F., et al., "Factor Xa Activates Endothelial Cells by a Receptor Cascade Between EPR-1 and PAR-2," Arterioscler Thromb Vasc Biol., Nov. 2000; pp. 1-6.
Lala, P. et al, "Role of Nitric Oxide in tumor progression: Lessons Learned from Experimental Tumors," Cancer and Metastasis Review, vol. 17, pp. 91-106 (1998).
Golub, T., et al., Molecular Classification of Cancer Science (1999), vol. 286, 531-537.
FDA mulls drug to slow late-stage Alzheimer's [online], [retrieved on Sep. 23, 2003]. Retrieved from the internet, URL:http://www.cnn.com/2003/HEALTH/conditions/09/24/alzheimers.drug.ap/index.html>.
Ullman's Encyclopedia of Industrial Chemistry, Fifth Revised Ed., Editors: Elvers, B., Hawkins, S., VCH Verlagsgesellschaft mbH, Weinheim, 19985-1996, Ch. 5, 488-506.
Zhu, B., Scarborough, R., "Recent Advances in Inhibitors of Factor Xa in the Prothrombinase Complex," Curr. Opinions Card. Pul. Ren. Inv. Drugs, 1:63-87 (1999).
Uzan, A., "Antithrombotic Agents," Emerging Drugs: The Prospect for Improved Medicines, 3: 189-208 (1998).
Kaiser, B., "Thrombin and Factor Xa Inhibitors," Drugs of the Future, 23: 423-426 (1998).
Al-Obeidi, F., Ostrem, J., "Factor Xa Inhibitors," Expert Opin. Therapeutic Patents, 9: 931-953 (1999).
Al-Obeidi, F., Ostrem, J., "Factor Xa Inhibitors by Classical and Combinatorial Chemistry," DDT, 3: 223-231 (May 1998).
Hauptmann, J.,et al., "Synthetic Inhibitors of Thrombin and Factor Xa: From Bench to Bedside," Thrombosis Research , 93: 203-241 (1999).
Becker, M.R., et al., "Synthesis, Sar and in Vivo Activity of Novel Thienopyridine Sulfonamide Pyrrolidininones as Factor Xa Inhibitors," Bioorganic and Medicinal Chemistry Letters, 9: 2753-2758 (1999).
Linder, J., et al., "Delayed Onset of Inflammation in Protease-Activated Receptor-2-Deficient Mice," J. Immunology, 2000, pp. 6504-6510.
Cirino, G. et al. Inflammation-Coagulation Network: Are Serine Protease receptors the knot?; Tips; 200, vol. 21, pp. 170-172.
Roehrig, S. et al. Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor. J. Med. Chem. 48, 22. Sep. 2005, pp. 5900-5908.
Caira, M. Crystalline Polymorphism of Organic Compounds. Springer Verlag Berlin Heidelberg 198, 1998, pp. 163-208.
Hancock, B. et al. Characteristics and Significance of the Amorphous State in Pharmaceutical Systems. Journal of Pharmaceutical Science. 86, 1 (1997-1), pp. 1-12.
Chiou, W.L. et al. Pharmaceutical Applications of Solid Dispersion Systems. Journal of Pharmaceutical Sciences 60, (1971). 128-1302.
Ford, J.L. The Current Status of Solid Dispersions. Pharm Acta Helv. 61, (1986)69-88.
Rasenack, N. et al. Poorly Water-soluble Drugs for Oral Delivery—A Challenge for Pharmaceutical Development. Pharmazeutische Industrie 67, Nr. 5 (2005), 583-591.
Breitenbach, J. Melt extrusion: from process to drug delivery technology. European Journal of Pharmaceutics and Biopharmaceutics 54 (2002) 107-117.
http://familydoctor.org/online/famdocen/home/common/heartdisease/basics/290.html.
Lerk, et al., Effect of Hydrophilization Drugs on Release Rat from Capsules, J. of Pharma. Sciences, 67(7), pp. 935-939 (1978).
Lerk, et al., In Vitro and In Vivo Availability of Hydrophilized Phenytoin from Capsules, J. of Pharma. Sciences, 68(5), pp. 634-638 (1979).
Greaves, et al., Novel Approaches to the Preparation of Low-Dose Solid Dosage Forms,Pharmaceutical Technology. January, pp. 60-64, (1995).
Reppe, et al., Justus Liebigs Ann. Chem. 596, 1955, p. 209.
Wong et al., The Journal of Pharmacology and Expermental Therapeutics, vol. 295, No. 1 (2000) pp. 212-218.
[Database Bielstein] Bielstein Institute for Organic Chemistry, Frankfurt-Main, DE. Database Accession No. 8822985.
Perzborn, E. et al. In vitro and in vivo studies of the novel antithrombotic agent BAY 59-7939—an oral, direct Factor Xa inhibitor. Journal of Thrombosis and Haemostasis 3, 3, Mar. 2005, pp. 514-521.
Espinosa, G. et al. Thrombotic microangiopathic haemolytic anaemia and antiphospholipid antibodies. Annals of the Rheumatic Diseases, 63, 6, Jun. 2004, pp. 730-736.
Bonomini, V. et al. A New Antithrombotic Agent in the Treatment of Acute Renal Failure Due to Hemolytic-Uremic Syndrome and Thrombotic Thrombocytopenic Purpura. Nephron 37, 1984, 2, 144.
Sinha, U. et al. Antithrombotic and hemostatic capacity of factor Xa versus thrombin inhibitors in models of venous and arteriovenous thrombosis. European Journal of Pharmacology 2000, 395, 51-59.
Betz, A. Recent advances in Factor Xa inhibitors. Expert Opinion Ther. Patents 2001, 11, 1007-1017.
Ruef, J. et al. New antithrombotic drugs on the horizon. Expert Opinion Investig. Drugs 2003, 12, 781-797.
Samama, M.L. Synthetic direct and indirect factor Xa inhibitors. Thromobis Research 2002, 106, V267-V273.
Quan, M.L. The race to an orally active Factor Xa inhibitor: Recent advances. Current Opinion in Drug Discovery & Development 2004, 7, 460-469.
The Ephesus Study, Blood 2000, 96, 490a.
The Penthifra Study, Blood 2000, 96, 490a.
The Pentamaks Study, Blood 2000, 96, 490a-491a.
The Pentathlon 2000 Study, Blood 2000, 96, 491a.
Leadley, R.J. Coagulation Factor Xa Inhibition: Biological Background and Rationale. Current Topics in Medical Chemistry 2001, 1, 151-159.

(56) References Cited

OTHER PUBLICATIONS

Gilligan, D.M. et al. The Management of Atrial Fibrillation. The American Journal of Medicine, vol. 101, (4) 1996, 413-421.
Kubitza, D. et al. Novel factor Xa inhibitors for prevention and treatment of thromboembolic diseases. Expert Opinion on Investig. Drugs, vol. 15, (8) 2006, pp. 843-855.
Williams, E.M. Vaughan. Classificating anti-arrhythimic drugs. In: Cardiac Arrythias-Proceedings of a symposium, sandoe E., soedertaeje: Astra (1970), pp. 449-469.
Breitenbach, J. Feste Loesungen durch Schmelzextrusion-ein integriertes Herstellkonzept. Pharmazie in unserer Zeit 29 (2000), 46-49.
Pschyrembel, Klinisches Worterbuch, 257. Auflage, 1994, Walter de Gruyter Verlag, p. 610, Stichwort "Heparin."
Pschyrembel, Klinisches Worterbuch, 257. Auflage, 1994, Walter de Gruyter Verlag, p. 292, Stichwort "Cumarinderivate."
Pschyrembel, Klinisches Worterbuch, 257. Auflage, 1994, Walter de Gruyter Verlag, p. 199-200, Stichwort "Blutgerinnung."
Rompp Lexikon Chemie, Ver. 1.5, 1998, Georg Thieme Verlag Stuttgart, Stichwort "Heparin."
Rompp Lexikon Chemie, Ver. 1.5, 1998, Georg Thieme Verlag Stuttgart, Stichwort "Blutgerrinung" Lubert Stryer, Biochemie, Spektrum der Wissenschaft Verlagsgesellschaft mbH Heidelberg, 1990, p. 259.
Substantiation of the Opposition, Application/Patent: 06706291.9/ EP 1 845 961 B1, "Treatment of Thromboembolic Disorders With Rivaroxaban," (Dec. 30, 2015), Henkel, Breuer & Partner, pp. 1-25.
Statement of Opposition, Application/Patent: 06706291.9/EP 1 845 961 B1, "Treatment of Thromboembolic Disorders With Rivaroxaban," (Jan. 6, 2016), Elkington and Fife LLP, Opponent: Actavis Group PTC ehf, pp. 1-12.
Notice of Opposition to a European Patent, Application/Patent: 06706291.9/EP 1 845 961 B1, "Treatment of Thromboembolic Disorders With Rivaroxaban," (Jan. 21, 2016), Opponent: Abdi Ibrahim Ilac Sanayi ve Ticaret A.S., pp. 1-9.
Statement of Grounds for Opposition, Application/Patent: 06706291.9/EP 1 845 961 B1, "Treatment of Thromboembolic Disorders With Rivaroxaban," (Jan. 21, 2016), Opponent: Generics Ltd.; Elend, Almut Susanne Authorised Representative, pp. 1-10.
The Opposition patent, Application/Patent: 06706291.9/EP 1 845 961 B1, "Treatment of Thromboembolic Disorders With Rivaroxaban," (Jan. 21, 2016), Opponent: Alexander Wittkopp, pp. 1-14.
Opposition, Application/Patent: 06706291.9/EP 1 845 961 B1, "Treatment of Thromboembolic Disorders With Rivaroxaban," (Jan. 21, 2016), Opponent: STADA Arzneimittel AG, and an English Translation, pp. 1-27.
Opposition, Application/Patent: 06706291.9/EP 1 845 961 B1, "Treatment of Thromboembolic Disorders With Rivaroxaban," (Jan. 21, 2016), Opponent: Teva Pharmaceutical Industries Ltd, pp. 1-14.
Statement of Opposition, Application/Patent: 06706291.9/EP 1 845 961 B1, "Treatment of Thromboembolic Disorders Vith Rivaroxaban," (Jan. 21, 2016), Opponent: Zaklady Farmaceutyczne Polpharma SA, pp. 1-12.
Opposition, Application/Patent: 06706291.9/EP 1 845 961 B1, "Treatment of Thromboembolic Disorders With Rivaroxaban," (Jan. 22, 2016), Opponent: ABG Patentes, S.L., pp. 1-22.
Opposition, Application/Patent: 06706291.9/EP 1 845 961 B1, "Treatment of Thromboembolic Disorders With Rivaroxaban," (Jan. 22, 2016), Opponent: Galenicum Health S.L., pp. 1-19.
Opposition, Application/Patent: 06706291.9/EP 1 845 961 B1, "Treatment of Thromboembolic Disorders With Rivaroxaban," (Jan. 22, 2016), Opponent: Hexal AG, pp. 1-12.
Opposition, Application/Patent: 06706291.9/EP 1 845 961 B1, "Treatment of Thromboembolic Disorders With Rivaroxaban," (Jan. 22, 2016), Opponent: Kraus&Weisert, pp. 1-11.
Opposition, Application/Patent: 06706291.9/EP 1 845 961 B1, "Treatment of Thromboembolic Disorders With Rivaroxaban," (Jan. 22, 2016), Opponent: Stolmár & Partner IP, pp. 1-9.
Aulton, "Pharmaceutics the Science of Dosage Form Design," Second Edition, Churchill Livingstone, (2002), pp. 410-411.
Lieberman et al., "Pharmaceutical Dosage Forms Tablets," Second Edition, Revised and Expanded, Marcel Dekker, Inc., (1989), p. 131. (3 Pages).
Foster et al., "Basic Pharmacology," University of Manchester, Department of Pharmacology, Materia Medica and Therapeutics, (1980), pp. 255 (3 pages).
Xarelto Dosing and Transition Management, Janssen Pharmaceuticals, Inc., (Apr. 2015), pp. 1-3.
Goodman & Gilman's, "The Pharmacological Basis of Therapeutics," 10th Edition, (edited by Joel G. Hardman, Lee E. Limbird, Alfred Goodman Gilman, Chapter 1, (2001), pp. 1-29.
Rote Liste, (2004), Clexane (Enoxaparin-Natrium), pp. 20. (3 pages).
Kubitza et al., "Multiple does Escalation Study Investigating BAY 59-7939 an Oral, Direct Factor Xa Inhibitor—in Healthy Male Subjects," (PO080), Pathophysiol Haemost Thromb, (2003), vol. 33 (suppl2), pp. 98.
Kubitza et al., "Single dose Escalation Study of BAY 59-7939—an Oral, Direct Factor Xa Inhibitor—in Healthy Male Subjects," (PO081), Pathophysiol Haemost Thromb, (2003), vol. 33 (suppl2), pp. 98.
Fareed et al., "Pharmacodynamic and Pharmacokinetic Properties of Enoxaparin," Clin Pharmacokinet, (2003), vol. 42, No. 12, pp. 1043-1057.
Harder et al., "Effects of BAY 59-7939, an Innovative, Oral, Direct Factor Xa Inhibitor, on Thrombin Generation in Healthy Volunteers," (PO078), Pathophysiol Haemost Thromb, (2003), vol. 33 (suppl2), pp. 97.
Ritschel et al., "Die Tablette Handbuch der Entwicklung, Herstellung und Qualitätssicherung," Aulendorf: ECV—Editio-Cantor-Verl., (2002). 3 pages.
Kearon, "Duration of Venous Thromboembolism Prophylaxis After Surgery," Chest (2003), vol. 124, pp. 386S-392S.
Derendorf et al., "Pharmakokinetik Einführung in die Theorie und Relevanz Für die Arzneimitteltherapie," Wissenschaftliche Verlagsgesellschaft mbH Stuttgart, (2002), pp. 1-23.
Weinz et al., "In Vitro Metabolism of Bay 59-7939—An Oral, Direct Factor Xa Inhibitor," (195), Drug Metabolism Review, (2004), vol. 36, Issue 1 Supplement, Abstracts from the 7th International ISSX Meeting, pp. 98.
Vrijens et al., "Non-Vitamin K Antagonist Oral Anticoagulants: Considerations on Once- Vs. Twice-Daily Regimens and their Potential Impact on Medication Adherence," Europace, (2015), vol. 17, pp. 514-523.
Oberpichler-Schwenk: "Rivaroxaban", Medizinische Monatsschrift für Pharmazeuten, (2008), vol. 31, No. 11, pp. 412-416.
European Pharmacopeia, 5th edition, Jun. 15, 2004, 2.9.3 Dissolution Test for Solid Dosage Forms, pp. 1-4.
Birkett, "Pharmacokinetics made easy 11 Designing dose Regimens," Aust Prescr, (1996), vol. 19, pp. 76-79. (6 pages).
Hospira UK Ltd and Genentech Inc, dated Apr. 10, 2014, Neutral Citation No. [2014] EWHC 1094 (Pat), pp. 1-47.
EU Clinical Trials Register, EudraCT No. 2004-002171-16 (Sweden), Nov. 17, 2004, https:/ /www.clinicaltrialsregister.eu/ctr-search/trial/2004-002171-16/SE, pp. 1-5.
Rowland et al., "Clinical Pharmacokinetics, concepts and applications", 3rd Edition, Lea and Febiger, Philadelphia (1995), (Why Clinical Pharmacokinetics?), pp. 1-7.
Patrono et al., "Platelet-Active Drugs the Relationships among Dose, Effectiveness, and Side Effects," Chest, (Jan. 2001), vol. 119, No. 1, pp. 39S-63S.
Mueck et al., "Clinical Pharmacokinetic and Pharmacodynamic Profile of Rivaroxaban," Clin Pharmacokinet, (2014), vol. 53, pp. 1-16.
ClinicalTrials.gov, Dose-ranging Study of Once-daily Regimen of BAY 59-7939 in the Prevention of VTE in Patients Undergoing Elective Total Hip Replacement (ODIXaHIP-0D), https://clinicaltrials.gov/ct2/show/study/NCT00396786#wrapper, pp. 1-3; accessed Nov. 1, 2016.

(56) References Cited

OTHER PUBLICATIONS

Charbonnier et al., "Comparison of a once daily with a twice daily subcutaneous low molecular weight heparin regimen in the treatment of deep vein thrombosis. FRAXODI group," Thromb Haemost, (May 1998), vol. 79, No. 5, pp. 897-901. (Abstract Only).

Turpie et al., "BAY 59-7939: an Oral, Direct Factor Xa Inhibitor for the Prevention of Venous Thromboembolism in Patients after total Knee Replacement. A Phase II Dose-Ranging Study," Journal of Thrombosis and Haemostasis, (2005), vol. 3, pp. 2479-2486.

Kubitza et al., "Safety, Pharmacodynamics, and Pharmacokinetics of Single Doses of BAY 59-7939, an Oral, Direct Factor Xa Inhibitor," Clinical Pharmacology & Therapeutics, (2005), vol. 78, No. 4, pp. 412-421.

Griffin et al., "The Textbook pf Pharmaceutical Medicine," 4th Edition, BMJ Books (2002), pp. 225-226, 238-239. (6 pages).

U.S. Pharmacopeia, General Chapters: <1088> In Vitro and In Vivo Evaluation of Dosage Forms, http://www.pharmacopeia.cn/v29240/usp29nf24s0_cl088.htm, pp. 1-17; accessed Jan. 21, 2016.

Harron et al., "Bopindolol a Review of its Pharmacodynamic and Pharmacokinetic Properties and Therapeutic Efficacy," Drugs, (1991), vol. 41, No. 1, pp. 130-149.

Clinical Pharmacology and Biopharmaceutics Review(s), Center for Drug Evaluation and Research, Application No. 0224060rig1s000; 2009, pp. 1-139.

Cleveland Clinic Pharmacotherapy Update, "Enoxaparin Clinical Pearl", vol. VI, No. 1, Jan./Feb. 2003, http://www.clevelandclinicmeded.com/medicalpubs/pharmacy/janfeb2003/enoxaparin.htm, pp. 1-2.

Fareed et al., "Studies on the Mechanism of Action of BAY 59-7939—an Oral, Direct Factor Xa Inhibitor," (PO077), Pathophysiol Haemost Thromb, (2003), vol. 33 (suppl2), pp. 97.

Lieberman et al., "Pharmaceutical Dosage Forms," Tablets, (1980), vol. 1, Marcel Dekker, pp. 172-181; (7 pages).

Mattsson: "Pharmaceutical Binders and Their Function in Directly Compressed Tablets—Mechanistic Studies on the Effect of Dry Binders on Mechanical Strength, Pore Structure and Disintegration of Tablets"; Comprehensive Summaries of Uppsala Dissertations from the Faculty of Pharmacy, 238, ACTA Universitatis Upsaliensis Uppsala 2000, pp. 1-62.

Rasenack et al., "Crystal Habit and Tableting Behavior," International Journal of Pharmaceutics, (2002), vol. 244, pp. 45-57.

PREVENTION AND TREATMENT OF THROMBOEMBOLIC DISORDERS

The present invention relates to the field of blood coagulation, more specifically it relates to a method of treating a thromboembolic disorder by administering a direct factor Xa inhibitor once daily in oral dosage form to a patient in need thereof, wherein the factor Xa inhibitor has a plasma concentration half life indicative of a bid or tid administration interval, e.g. of 10 hours or less.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic pathways, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin, a fibrous/gelatinous coagulant. In addition, thrombin is a potent effector of platelet aggregation which likewise contributes significantly to haemostasis.

Maintenance of normal haemostasis—the balance between bleeding and thrombosis—is subject to a complex regulatory mechanism. Uncontrolled activation of the coagulant system or defective inhibition of the activation processes may cause formation of local thrombi or embolisms in vessels (arteries, veins) or in heart cavities. This may lead to serious disorders, such as myocardial infarction, angina pectoris (including unstable angina), vascular re-occlusions and restenoses after angioplasty or aortocoronary bypass, stroke, transitory ischaemic attacks, peripheral arterial occlusive disorders, pulmonary embolisms or deep vein thromboses; herein below, these disorders are collectively also referred to as thromboembolic disorders. In addition, in the case of consumption coagulopathy, hypercoagulability may—systemically—result in disseminated intravascular coagulation.

These thromboembolic disorders are the most frequent cause of morbidity and mortality in most industrialised countries. Estimates place the annual incidence of VTE in excess of 1 case per 1,000 persons [White, R. H. The epidemiology of venous thromboembolism. Circulation 107 (Suppl. 1), 14-18 (2003)]. About 1.3-4.1 persons in 1,000 experience a first stroke [Feigin, V. L., Lawes, C. M., Bennett, D. A., Anderson, C. S. Lancet Neurol. 2, 43-53 (2003)], and about 5 in 1,000 persons a myocardial infarction annually [Fang, J, Alderman, M. H. Am. J. Med 113, 208-214 (2002)].

The anticoagulants, i.e. substances for inhibiting or preventing blood coagulation, which are known from the prior art have various, often severe disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally (intravenously or subcutaneously). Owing to more favourable pharmacokinetic properties, preference is nowadays more and more given to low-molecular-weight heparin. Since heparin inhibits a plurality of factors of the blood coagulation cascade at the same time, the action is non-selective. Moreover, there is a high risk of bleeding.

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a non-selective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required.

Recently, a novel therapeutic approach for the treatment and prophylaxis of thromboembolic disorders has been described. This novel therapeutic approach aims to inhibit factor Xa [cf. WO-A-99/37304; WO-A-99/06371; J. Hauptmann, J. Stürzebecher, Thrombosis Research 1999, 93, 203; S. A. V. Raghavan, M. Dikshit, "Recent advances in the status and targets of antithrombotic agents" Drugs Fut. 2002, 27, 669-683; H. A. Wieland, V. Laux, D. Kozian, M. Lorenz, "Approaches in anticoagulation: Rationales for target positioning" Curr. Opin. Investig. Drugs 2003, 4, 264-271; U. J. Ries, W. Wienen, "Serine proteases as targets for antithrombotic therapy" Drugs Fut. 2003, 28, 355-370; L.-A. Linkins, J. I. Weitz, "New anticoagulant therapy" Annu. Rev. Med. 2005, 56, 63-77]. It has been shown that, in animal models, various both peptidic and nonpeptidic compounds are effective as factor Xa inhibitors.

In general, oral application is the preferable route of administration of a drug, and a less frequent dose regimen is desirable. In particular, once daily oral application is preferred due to favourable convenience for the patient and for compliance reasons. However, this goal is sometimes difficult to achieve depending on the specific behaviour and properties of the drug substance, especially its plasma concentration half life. "Half life" is the time it takes for the plasma concentration or the amount of drug in the body to be reduced by 50% (Goodman and Gillmans "The Pharmacological Basis of Therapeutics" 7th Edition, Macmillan Publishing Company, New York, 1985, p 27).

When the drug substance is applied in no more than a therapeutically effective amount, which is usually preferred in order to minimize the exposure of the patient with that drug substance in order to avoid potential side effects, the drug must be given approximately every half live (see for example: Malcolm Rowland, Thomas N. Tozer, in "Clinical Pharmacokinetics, Concepts and Applications", 3rd edition, Lea and Febiger, Philadelphia 1995, pp 83).

In the case of multiple dose application the target plasma concentration (approximate steady state) can be reached after 3 to 5 half lives (Donald J. Birkett, in "Pharmacokinetics Made Easy", McGraw-Hill Education: 2000; p 20). At steady state the concentrations of drugs which rise and fall during each interdose interval are repeated identically in each interdose interval (Goodman and Gillmans "The Pharmacological Basis of Therapeutics" 7th Edition, Macmillan Publishing Company, New York, 1985, p 28).

Surprisingly, it has now been found in patients at frequent medication that once daily oral administration of a direct factor Xa inhibitor with a plasma concentration half life time of 10 hours or less demonstrated efficacy when compared to standard therapy and at the same time was as effective as after twice daily (bid) administration.

Therefore, the present invention relates to a method of treating a thromboembolic disorder comprising administering a direct factor Xa inhibitor no more than once daily for at least five consecutive days in an oral dosage form to a patient in need thereof, wherein said inhibitor has a plasma concentration half life of 10 hours or less when orally administered to a human patient.

The present invention further relates to the use of an oral dosage form of a direct factor Xa inhibitor for the manufacture of a medicament for the treatment of a thromboembolic disorder administered once daily for at least five consecutive days, wherein said inhibitor has a plasma concentration half life of 10 hours or less when orally administered to a human patient.

In a preferred embodiment, the present invention relates to 5-Chloro-N-({(5S)-2-oxo-3-[4-(3-oxo-4-morpholinyl)-phenyl]-1,3-oxazolidin-5-yl}-methyl)-2-thiophenecarboxamide (I), a low molecular weight, orally administrable direct inhibitor of blood clotting factor Xa (see WO-A 01/47919, whose disclosure is hereby included by way of reference) as the active ingredient.

Compound (I) is an active site directed, competitive, direct factor Xa inhibitor [E. Perzborn, J. Strassburger, A. Wilmen, J. Pohlmann, S. Roehrig, K.-H. Schlemmer, A. Straub; *J Thromb Haemost* 2005; DOI: 10.1111/j.1538-7836.2005.01166.x]. (I) acts directly on factor Xa, that means independently from a cofactor (such as Antithrombin III, the cofactor of heparins). The antithrombotic effect is attributed to the inhibition of factor Xa.

Furthermore, (I) binds to the active site of factor Xa in the S1- and S4 pockets [S. Roehrig et al. 228th ACS National Meeting, Philadelphia, Aug. 22-26, 2004, MEDI-156].

For (I) a plasma concentration half life of 4-6 hours has been demonstrated at steady state in humans in a multiple dose escalation study (D. Kubitza et al, Multiple dose escalation study investigating the pharmacodynamics, safety, and pharmacokinetics of Bay 59-7939, an oral, direct Factor Xa inhibitor, in healthy male subjects. Blood 2003, 102: Abstract 3004)

In a clinical study in patients undergoing total hip replacement (THR), the efficacy of (I) is measured by the occurrence of deep vein thrombosis (DVT) after THR surgery. According to the Sixth ACCP Consensus Conference on Antithrombotic Therapy (Chest 2001; 119: 132S-175S) the DVT rate (prevalence) after THR surgery is as follows:

|  | Prevalence (%) | (95% Confidence interval) |
| --- | --- | --- |
| Placebo | 54.2 | (50-58) |
| Low dose heparin | 30.1 | (27-33) |
| LMWH* | 16.1 | (15-17) |

*LMWH = Low Molecular Weight Heparin

After 7 to 9 days of once daily administration of 30 mg (I) to 73 patients undergoing THR surgery, a DVT rate of 12.3% has been observed (LMWH comparator was 16.8%). Administration of (I) was also safe and well tolerated.

The once daily dose of (I) was also compared to different doses of (I) which have been administered twice daily (bid). By comparing the total daily doses administered it could also be demonstrated that after once daily administration efficacy on one hand and major bleeding, an expected side effect on the other hand, match well the expected effects after twice daily administration (for a discussion of further details see the experimental part).

The present invention further relates to a packaged pharmaceutical composition comprising a container containing a rapid-release tablet comprising 5-Chloro-N-({(5S)-2-oxo-3-[4-(3-oxo-4-morpholinyl)phenyl]-1,3-oxazolidin-5-yl}methyl)-2-thiophenecarboxamide, said container furthermore containing instructions for using said rapid-release tablet to treat a thromboembolic disorder.

In a preferred embodiment, said packaged pharmaceutical composition, comprising a container containing a rapid-release tablet comprising 5-Chloro-N-({(5S)-2-oxo-3-[4-(3-oxo-4-morpholinyl)phenyl]-1,3-oxazolidin-5-yl}methyl)-2-thiophenecarboxamide, said container furthermore containing instructions for administering said rapid-release tablet at a frequency of once daily.

In another preferred embodiment, the present invention relates to one of the following compounds:

AX-1826 [S. Takehana et al. *Japanese Journal of Pharmacology* 2000, 82 (Suppl. 1), 213P; T. Kayahara et al. *Japanese Journal of Pharmacology* 2000, 82 (Suppl. 1), 213P]

HMR-2906 [XVIIth Congress of the International Society for Thrombosis and Haemostasis, Washington D.C., USA, 14-21 Aug. 1999; Generating greater value from our products and pipeline. Aventis SA Company Presentation, 5 Feb. 2004]

Otamixaban (FXV-673, RPR-130673) [V. Chu et al. *Thrombosis Research* 2001, 103, 309-324; K. R. Guertin et al. *Bioorg. Med. Chem. Lett.* 2002, 12, 1671-1674]

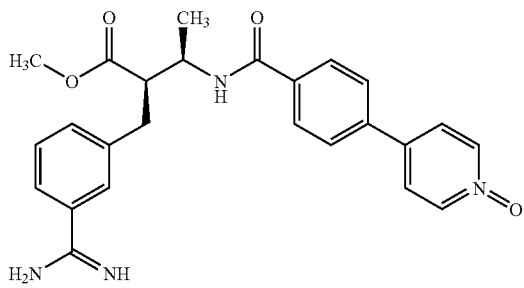 [SMILES: COC(=O)[C@H](Cc1cccc(C(=N)N)c1)[C@@H](C)NC(=O)c1ccc(-c2cc[n+]([O-])cc2)cc1]

BIBT-986 (prodrug: BIBT-1011) [American Chemical Society—226th National Meeting, New York City, N.Y., USA, 2003]

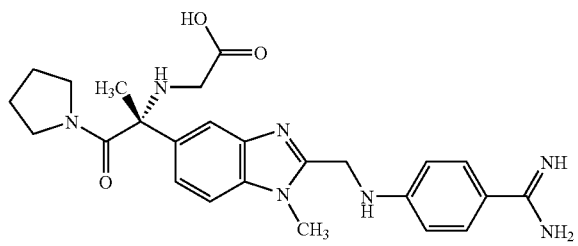 [SMILES: Cn1c(CNc2ccc(C(=N)N)cc2)nc2cc([C@@](C)(NCC(=O)O)C(=O)N3CCCC3)ccc21]

DPC-602 [J. R. Pruitt et al. *J. Med. Chem.* 2003, 46, 5298-5313]

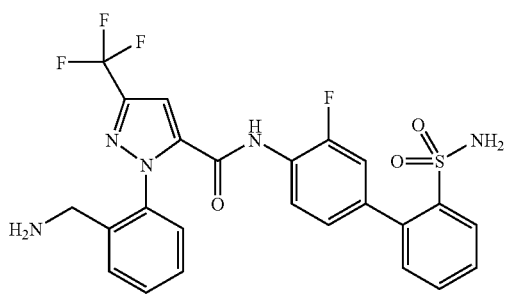 [SMILES: NCc1ccccc1-n1nc(C(F)(F)F)cc1C(=O)Nc1ccc(-c2ccccc2S(N)(=O)=O)cc1F]

DX-9065a [T. Nagahara et al. *J. Med. Chem.* 1994, 37, 1200-1207]

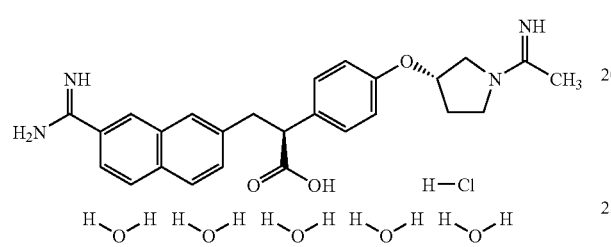

DU-176b [Y. Morishima et al. *Blood* 2004, 104, 11, ASH 2004 (Abst 1862); T. Fukuda et al. *Blood* 2004, 104, 11, ASH 2004 (Abst 1852); T. Furugohri et al. *Blood* 2004, 104, 11, ASH 2004 (Abst 1851)]

813893 [Proteinase Inhibitor Design—Fourth SCI-RSC Symposium, Proteinase 2004: Strategies for New Medicines (Part I), London]

KFA-1982 (prodrug of KFA-1829) [T. Koizumi et al. *Journal of Thrombosis and Hemostasis* 2003, 1 Suppl 1, P2022]

M-55532 [H. Nishida et al. 228th ACS National Meeting, Philadelphia, Aug. 22-26, 2004, MEDI-251; H. Nishida et al. *Chem. Pharm. Bull.* 2004, 52, 406-412, dito 459-462]

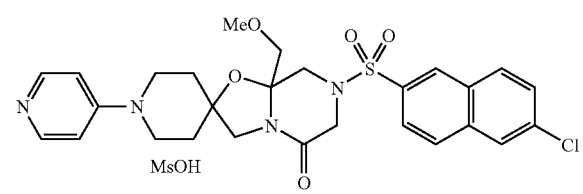

M-55555 [H. Nishida et al. 16th Int Symp Med Chem, Bologna, 18-22 Sep. 2000, Abst PA-125]

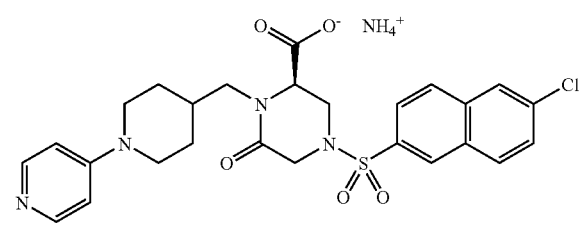 [SMILES: O=C([O-])[C@H]1CN(S(=O)(=O)c2ccc3cc(Cl)ccc3c2)CC(=O)N1CC1CCN(c2ccncc2)CC1 ; [NH4+]]

M-55551 [H. Nishida et al. *Chem. Pharm. Bull.* 2002, 50, 1187-1194]

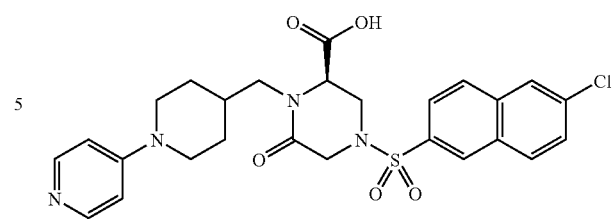

M-55190 [H. Nishida et al. 16th Int Symp Med Chem, Bologna, 18-22 Sep. 2000, Abst PA-125]

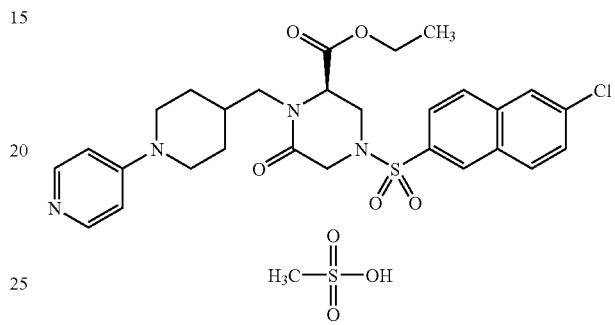

M-55113 [H. Nishida et al. *Chem. Pharm. Bull.* 2001, 49, 1237-1244]

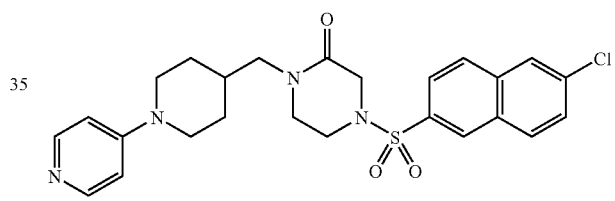

LY517717 [S. Young, Medicinal Chemistry-12th RSC-SCI Symposium, 7-10 Sep. 2003, Cambridge, UK; M. Wiley et al. 228th ACS National Meeting, Philadelphia, Aug. 22-26, 2004, MEDI-252 & 254]

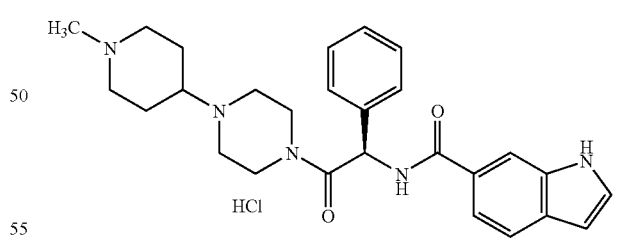

YM-150 [Research and development pipeline. Yamanouchi Pharmaceutical Co Ltd, Company World Wide Web site, 11 February 2004]

In another preferred embodiment, the present invention relates to direct active site directed factor Xa-inhibitors which bind to the active site of factor Xa in the S1- and S4 pockets as does (I). Such a binding mode is also reported for compounds cited in the following references whose disclosure, preferentially the compounds disclosed therein, is hereby included by way of reference:

M. Nazare et al. Bioorg. Med. Chem. Lett. 2004, 14, 4191-4201; dito 2801-2805; Y.-M. Choi-Sledeski et al. J. Med. Chem. 2003, 46, 681-690;

M. Adler et al. Biochemistry 2002, 41, 15514-15523; Y. L. Chou et al. Bioorg. Med. Chem. Lett. 2003, 13, 507-511;

M. L. Quan et al. J. Med. Chem. 2004, online ASAP jm0497949; DPC602: J. R. Pruitt et al. J. Med. Chem. 2003, 46, 5298-5313; DPC 423: D. J. P. Pinto et al. J. Med. Chem. 2001, 44, 566-578;

N. Haginoya, J. Med. Chem. 2004, 47, 5167-5182;

S. Young, Medicinal Chemistry—12th RSC-SCI Symposium, 7-10 Sep. 2003, Cambridge, UK; M. Wiley et al. 228th ACS National Meeting, Philadelphia, Aug. 22-26, 2004, MEDI-252 & 254;

W. W. K. R. Mederski et al. Bioorg. Med. Chem. Lett. 2004, 14, 3763-3769;

P. Zhang et al. Bioorg. Med. Chem. Lett. 2004, 14, 983-987, dito 989-993;

H. Nishida et al. Chem. Pharm. Bull. 2004, 52, 406-412, dito 459-462;

J. A. Willardsen et al. J. Med. Chem. 2004, 47, 4089-4099.

For the purpose of the present invention as disclosed and described herein, the following terms and abbreviations are defined as follows.

The term "treatment" includes the therapeutic and/or prophylactic treatment of thromboembolic disorders.

The term "direct factor Xa inhibitor" means an inhibitor that acts directly on factor Xa, independently of a cofactor (such as Antithrombin III, the cofactor of heparins). The antithrombotic effect is hereby attributed to the inhibition of factor Xa.

The term "thromboembolic disorders" includes in particular disorders as the acute coronary syndrome spectrum as ST Segment Elevation Myocardial Infarction (STEMI) (also known as Q-wave MI), Non ST Segment Elevation Myocardial Infarction (NSTEMI) (also known as Non Q-wave MI) and unstable angina (UA), as well as stable angina pectoris, vascular re-occlusions and restenoses after angioplasty or aorto-coronary bypass, peripheral arterial occlusion disorders, pulmonary embolisms, or deep vein thromboses, renal thrombosis, transitory ischaemic attacks and stroke, inhibition of tumor growth and development of metastasis, treatment of disseminated intravascular coagulation (DIC) and the so-called "economy class syndrome", especially in patients with risk of venous thrombosis, atherosclerotic diseases, inflammatory diseases, as rheumatic diseases of the musculoskeletal system, Alzheimer's disease, inhibition of old-age macula-degeneration, diabetic retinopathy, diabetic nephropathy and other microvascular diseases.

Included are also disorders derived from cardiogenic thromboembolism, for instance cerebral ischemic diseases, stroke, systemic embolism and ischemic attacks, especially in patients with acute, intermittent or persistent arrhythmia of the heart such as atrial fibrillation or alongside cardioversion, or in patients with valvular heart disease or artificial heart valves.

Moreover, included are also disorders derived from thromboembolic complications which can arise within patients with microangiopathic hemolytic anaemia, extracorporal circulation such as hemodialysis, or prosthetic heart valves as well as from thromboembolic complication, e.g. venous thromboembolism in tumor patients, in particular in patients undergoing surgical interventions, chemotherapy or radiotherapy.

Preferred is the treatment of acute coronary syndrome spectrum as ST Segment Elevation Myocardial Infarction (STEMI), Non ST Segment Elevation Myocardial Infarction (NSTEMI) and unstable angina, reocclusions after angioplasty or aortocoronary bypass, peripheral arterial occlusion disorders, pulmonary embolisms or deep vein thromboses, transitory ischaemic attacks and stroke.

Particularly preferred is the treatment of acute coronary syndrome spectrum as ST Segment Elevation Myocardial Infarction (STEMI), Non ST Segment Elevation Myocardial Infarction (NSTEMI) and unstable angina, reocclusions after angioplasty or aortocoronary bypass, pulmonary embolisms or deep vein thromboses and stroke.

The term "oral dosage forms" is used in a general sense to reference pharmaceutical products administered orally. Oral dosage forms are recognized by those skilled in the art to include such forms as liquid formulations, granules, gelcaps, hard gelatine capsules or sachets filled with granules, and tablets releasing the active compound rapidly or in a modified manner.

Tablets are preferred, in particular tablets rapidly releasing the active compound. In the context of the present invention, rapid-release tablets are in particular those which, according to the USP release method using apparatus 2 (paddle), have a Q value (30 minutes) of 75%.

Very particularly preferred are rapid-release tablets containing 5-Chloro-N-({(5S)-2-oxo-3-[4-(3-oxo-4-morpholinyl)-phenyl]-1,3-oxazolidin-5-yl}-methyl)-2-thiophenecarboxamide as active ingredient. Preparation of such tablets is for example described in PCT/04/01289, whose disclosure is hereby included by way of reference.

The amount of active ingredient in the formulation will depend on the severity of the condition, and on the patient to be treated, as well as the compound employed. In the case of (I) as active ingredient, a dose of 1 to 100 mg, preferentially 2 to 50 mg, particularly preferred 5 to 30 mg can be applied.

The term "once daily" is well known by those skilled in the art and means administration of the drug once a day and includes the administration of one dosage form as well as administration of two or more dosage forms simultaneously or consecutively within a short time period.

In a preferred embodiment, one oral dosage form is administered once daily.

The invention is illustrated, but in no way limited, by the following example:

EXPERIMENTAL PART

Clinical Trial

Example 1

This was a dose guiding study for the direct factor Xa inhibitor (I). Objective of the study was the assessment of safety, tolerability, and efficacy of (I) at different oral doses (bid and od) compared with subcutaneously administered enoxaparin 40 mg in the prevention of venous thromboembolism.

642 patients were enrolled in this study and the treatment duration was 7 to 9 days.

The main inclusion criteria for the study were: men ≥18 years of age and postmenopausal women undergoing elective primary total hip replacement.

This was a prospective, randomized, open-label, active comparator controlled, multi-center and multi-national trial designed as a proof-of-principle dose-escalating study in patients undergoing elective primary total hip replacement.

Patients were consecutively to receive within each dose step either (I) or the active comparator drug, enoxaparin:
one group receiving 2.5 mg (I) bid,
one receiving 5 mg (I) bid,
one receiving 10 mg (I) bid,
one receiving 20 mg (I) bid,
one receiving 30 mg (I) bid,
and one receiving 30 mg (I) od.

(I) was administered orally as rapid release tablets.
The criteria for evaluation were:
a) The primary efficacy endpoint was a composite endpoint of
   Any deep vein thrombosis (DVT) (proximal and/or distal).
   Non-fatal pulmonary embolism (PE).
   Death from all causes.
   The primary endpoint was evaluated 5-9 days after surgery. The analysis of the primary efficacy endpoint was solely based on the assessments made by the central adjudication committee which was blinded to the treatment allocation.
b) The main safety endpoint was the incidence of major bleeding events observed after the first intake of study drug and not later than 2 days after last intake of study drug. Major bleeding observed after this period was assessed separately.
   The analysis of the primary safety endpoint was solely based on the classification made by the Safety Committee and Bleeding Committee which were both blinded to the treatment allocation.

Results:

The analysis of demographic data can be summarized as follows:

For subjects in the "valid for safety analysis" age ranged from 30-92 years, weight from 45-150 kg, height from 145-195 cm, and BMI from 17.3-52.7 kg/m².

For subjects in the "valid for PP (per protocol) analysis" age ranged from 30-92 years, weight from 45-150 kg, height from 146-195 cm, and BMI from 17.3-37.7 kg/m².

a) Efficacy Results:
An 7-9-day treatment with (I) using a wide, 12-fold dose range [2.5 to 30 mg bid corresponding to total daily doses of 5 to 60 mg (I)] prevented venous thromboembolism (VTE) in adult subjects undergoing elective hip replacement compared with enoxaparin, thus confirming the proof-of-principle of (I) in this indication.

The reduction of the VTE incidence rates (primary composite endpoint comprising DVT, PE and death) by (I) was dose-dependent in the range from 2.5 to 20 mg bid with incidence rates declining from 22.2% to 10.2% compared with 16.8% in the enoxaparin group. The incidence rate in the mg od dose group was 15.1% (Table 1-1).

On the basis of total daily doses the 30 mg once daily dose fits well into the dose dependence observed in the range of 2.5 to 20 mg bid, which corresponds to total daily doses of 5 to 40 mg.

TABLE 1-1

Incidence rate of primary efficacy endpoint and its individual components (PP population)

|  | Dose (I) 2.5 mg bid (N = 63) | Dose (I) 5 mg bid (N = 63) | Dose (I) 10 mg bid (N = 55) | Dose (I) 30 mg od (N = 73) |
|---|---|---|---|---|
| Primary efficacy, | 14 (22.2%) | 15 (23.8%) | 11 (20.0%) | 11 (15.1%) |

TABLE 1-1-continued

Incidence rate of primary efficacy endpoint and its individual components (PP population)

composite endpoint [n (%)]

|  | Dose (I) 20 mg bid (N = 59) | Dose (I) 30 mg bid (N = 46) | Enoxaparin 40 mg od (N = 107) |
|---|---|---|---|
| Primary efficacy, composite endpoint [n (%)] | 6 (10.2%) | 8 (17.4%) | 18 (16.8%) |

Summary:
The above data clearly demonstrate the efficacy of od administration of (I), namely fewer occurrence of composite endpoint events, i.e. fewer cases of DVT, PE or death compared to untreated conditions, and in the range of standard therapy. Furthermore, the od administration is surprisingly perfect in line with bid administration.

b) Safety Results:
The number of post-operative major bleeding events increased with increasing (I) doses indicating a monotonous dose-response (table 1-2). However, it is important to note that there were neither fatal bleeds or bleeds in critical organs, nor clinically significant bleeds that could not be treated. Most bleeds adjudicated as major were related to the surgical site and no wound healing complications were reported in these subjects.

On the basis of total daily doses the 30 mg once daily dose fits very well into the dose dependence observed in the range of 2.5 to 30 mg bid which corresponds to total daily doses of 5 to 60 mg.

TABLE 1-2

Incidence rates of post-operative bleeding events (safety population)

|  | Dose (I) 2.5 mg bid (N = 76) | Dose (I) 5 mg bid (N = 80) | Dose (I) 10 mg bid (N = 68) | Dose (1) 30 mg od (N = 88) |
|---|---|---|---|---|
| Any major bleeding event [n (%)] | 0 (0.0%) | 2 (2.5%) | 2 (2.9%) | 4 (4.5%) |

|  | Dose (I) 20 mg bid (N = 77) | Dose (I) 30 mg bid (N = 74) | Enoxaparin 40 mg od (N = 162) |
|---|---|---|---|
| Any major bleeding event [n (%)] | 5 (6.5%) | 8 (10.8%) | 0 (0.0%) * |

* For LMWH in similar studies major bleeding rates of 1.5-5.3% have been observed (Sixth ACCP Consensus Conference on Antithrombotic Therapy, Chest 2001; 119: 132S-175S).

Summary:
The above data clearly demonstrate the safety of od administration of (I). The occurrence of any major bleeding events is low, approximately in the range of standard therapy and again perfectly in line with results from bid administration.

We claim:
1. A method of treating a thromboembolic disorder comprising
administering a direct factor Xa inhibitor that is 5-Chloro-N-({(5S)-2-oxo-3-[4-(3-oxo-4-morpholinyl)phenyl]-1,3-oxazolidin-5-yl}methyl)-2-thiophenecarboxamide no more than once daily for at least five consecutive days in a rapid-release tablet to a patient in need thereof, wherein the thromboembolic disorder is selected from the group consisting of pulmonary embolisms, deep vein thromboses, and stroke.

2. The method of claim 1, wherein the thromboembolic disorder is pulmonary embolisms.

3. The method of claim 1, wherein the thromboembolic disorder is deep vein thromboses.

4. The method of claim 1, wherein the thromboembolic disorder is stroke.

\* \* \* \* \*